United States Patent [19]
Insall et al.

[11] 4,213,209
[45] Jul. 22, 1980

[54] KNEE JOINT PROSTHESIS

[75] Inventors: John N. Insall, New York, N.Y.; Peter S. Walker, Ridgewood, N.J.

[73] Assignee: New York Society for the Relief of the Ruptured and Crippled, New York, N.Y.

[21] Appl. No.: 908,130

[22] Filed: May 22, 1978

[51] Int. Cl.² ............................................. A61F 1/24
[52] U.S. Cl. ..................................................... 3/1.911
[58] Field of Search ............................... 3/1.911, 1.91

[56] References Cited

U.S. PATENT DOCUMENTS

| | | | |
|---|---|---|---|
| 3,638,243 | 2/1972 | Campbell, Jr. et al. | 3/1.91 |
| 3,694,821 | 10/1972 | Moritz | 3/1.911 |
| 3,748,662 | 7/1973 | Helfet | 3/1.911 |
| 3,840,905 | 10/1974 | Deane | 3/1.911 |
| 3,869,729 | 3/1975 | Attenborough | 3/1.911 |
| 4,011,603 | 3/1977 | Steffee | 3/1.91 |
| 4,094,017 | 6/1978 | Matthews et al. | 3/1.911 |

FOREIGN PATENT DOCUMENTS

| | | | |
|---|---|---|---|
| 2531080 | 2/1976 | Fed. Rep. of Germany | 3/1.911 |
| 2288509 | 5/1976 | France | 3/1.911 |

OTHER PUBLICATIONS

Deane, G., "The Deane Knee A New Concept in Knee Joint Design," ©Instn. Mech. Engrs., 1975, pp. 140-143.
Attenborough, C. G., "Total Knee Replacement Using a Stabilised Gliding Prosthesis," ©Instn. Mech. Engrs., 1974, pp. 92-95.

*Primary Examiner*—Clifford D. Crowder
*Attorney, Agent, or Firm*—Brumbaugh, Graves, Donohue & Raymond

[57] ABSTRACT

A knee joint prosthesis comprises a femoral component having laterally spaced-apart condylar portions shaped to match generally the shapes of the condylar surfaces of the femur and a tibial component having a plate-like platform portion which includes laterally spaced-apart concavities in the external surface, each of which receives and supports one of the condylar portions of the femoral component in all positions of the leg. The femoral component has a box-like intercondylar portion interconnecting the condylar portions and defining an intercondylar recess which receives a post that extends upwardly from the tibial component. At and near full extension of the leg, any tendency for posterial dislocation of the femur results in engagement between the anterior surfaces of the post and recess to prevent posterial dislocation of the femoral component relative to the tibial component. At leg flexions approaching full flexure, the posterior surface of the recess engages the posterior surface of the post in the event of a tendency toward anterial dislocation of the femur, thereby preventing anterial dislocation. Large antero-posterior movements and dislocation are prevented in all leg positions by engagement between surfaces of the post and recess. The post and recess are shaped and dimensioned to permit essentially normal rotation and lateral angulation of the prosthetic joint in all positions.

4 Claims, 12 Drawing Figures

KNEE JOINT PROSTHESIS

BACKGROUND OF THE INVENTION

The development some years ago of a durable, non-toxic cement for connecting plastic and metal appliances to bone has made it possible to implant endoprosthetic devices in nearly every joint in the body, and such devices are becoming more and more widely used for reconstruction of joints that have been made painful, or in which function has been impaired, by disease or injury. A variety of designs of knee joint prostheses have been proposed, and some of those designs have proven to be highly successful after fairly considerable clinical experience.

The selection of a particular prosthesis for a knee joint is based largely on the condition of the patient's knee. In those instances in which there is little disease or injury of the bones, ligaments and other tissues, relatively simple components that require little resectioning of the bone and destruction of ligaments are preferred. At the other end of the scale are severely damaged joints which require implantation of components that will replace the condylar and patellar surfaces of the femur and most or all of the tibial plateau. Moreover, prostheses for use in severely damaged joints will often be constructed to impart stability to the joint by mechanical action of elements of the components.

The knee joint prosthesis described and shown in U.S. Pat. No. 3,837,009 (which is owned by the assignee of the present invention) is exemplary of the latter type of prosthesis. It includes a post that extends up from the tibial component into a slot in the femoral component and a pin or axle that is affixed to the femoral component and passes through a hole of carefully designed shape and size in the post. The coaction between the axle and the hole provides considerable stability by restraining movements (translational, angulational and rotational) of the tibial component relative to the femoral component. The forces transmitted between the axle and the hole can be very large, and they act at a relatively great distance from the tibial plateau; as a result, there is a fairly high degree of risk of the tibial component becoming dislodged from the tibia. A number of other known knee joint prostheses of the type that are designed to impart stability to the knee joint by mechanical action are similarly subject to failure. In some cases, the implantation of the prosthesis requires removal of a considerable amount of bone, and failure may include fracture of the remaining, weakened bone.

Between the two extremes of simple, small components (see, for example, U.S. Pat. No. 3,774,244, assigned to the assignee of the present invention) and prostheses constructed to have inherent mechanical stability is a relatively wide range of damaged knee joints in which most of the bone structure at the joint must be replaced but ligaments and other tissues that provide stability in the anatomical knee joint are undamaged or can be repaired so that essentially normal restraint and control of joint function are provided by remaining soft anatomical elements. Prostheses constructed for replacement of substantially all articulating surfaces of the bones at the joint are often referred to as "total" condylar joint prostheses, and a number of total knee joint prostheses of the condylar type have been proposed (see, for example, U.S. Pat. Nos. 3,748,662, 8,816,855 and 3,869,729). The assignee of the present invention has also developed a "total" condylar knee joint prosthesis that has been marketed for some time and is in widespread use.

Generally, a total knee joint prosthesis of the condylar replacement type includes a tibial component having a platform portion which replaces substantially all of the tibial plateau and substitutes for the anatomical tibial condylar surfaces. The femoral component has laterally spaced-apart condylar portions joined by an intercondylar bridge and a patellar surface and thus affords replacement of substantially all of the surfaces of the femur that engage the tibia and patella. Whether or not the cruciate ligaments are retained in a condylar replacement prosthesis depends on the design.

The total knee joint prostheses that have been proposed and used heretofore are generally highly successful in restoring reasonably normal function to a damaged or diseased knee joint, provided that they are of correct size and are properly implanted by the surgeon, particularly in respect of the register and reasonably precise axial location to ensure relatively normal function of the ligaments and muscles in imparting stability and function to the knee joint. On the other hand, the loss of the cruciate ligaments, which is necessary with some prostheses designs and may be required with some patients in any case, presents a higher risk of dislocation than exists in an anatomical knee joint in good condition. In addition, improper sizing or placement or the inability or failure to retain or restore adequate soft tissue support can result in impairment of function and loss of stability. For example, if after implantation, the ligaments are loose, which can occur if the joint has, in effect, shortened due to incorrect sizing or placement of the prosthesis, the prosthetic joint will be relatively unstable and subject to dislocation.

SUMMARY OF THE INVENTION

There is provided, in accordance with the present invention, a total knee joint prosthesis of the condylar type which is constructed to provide essentially free translation, rotation and angulation throughout most of the total range of articulation but to provide restraint and control at and near full extension and at the high end of the range of flexion.

More particularly, a knee joint prosthesis, according to the present invention, comprises a femoral component which includes a pair of laterally spaced-apart condylar portions having external surfaces that are smoothly curved in the anteroposterior direction generally to match in lateral profile the shapes of the condylar surfaces of the femur and smoothly convexly curved in all cross sections along their anteroposterior extents. The condylar portions are interconnected by a dome-like or box-like intercondylar portion which defines a recess that opens toward the tibial plateau and has spaced-apart lateral walls, an anterior surface and a posterior surface.

The tibial component of the prosthesis includes a plate-like platform portion having on its external or superior (as implanted) surface a pair of laterally spaced-apart concavities, each of which is shaped and dimensioned to receive and support in nested relation one of the condylar portions of the femoral component in all positions of the knee. A post extends upwardly from the superior surface of the tibial component between the concavities, into the intercondylar recess of the femoral component.

The relative positions and shapes of the anterior surfaces of the post of the tibial component and the intercondylar recess of the femoral component of the prosthesis as implanted in the knee joint are such that when the leg is extended and the femur tends to dislocate posteriorly relative to the tibia, the anterior surfaces of the post and recess engage each other and prevent posterial dislocation of the femoral component. Such dislocation is also prevented at the low end of the range of flexion. Over a large middle part of the range of flexion, the post and recess do not normally engage, and, therefore, relative antero-posterior translation within normal ranges is permitted without any engagement between the post and recess. On the other hand, extreme translation is prevented by engagement between the post and recess, and dislocation in either direction is prevented, unless there is a highly traumatic axial separation (which is extremely unlikely).

The posterior surfaces of the tibial post and femoral intercondylar recess are shaped and positioned such that in the prosthesis as implanted in the knee joint they engage each other in the range of from mid to full flexure under conditions which tend to dislocate the femur anteriorly, relative to the tibia, thus preventing anterial dislocation of the femoral component. Such engagement will normally occur as a matter of course beginning at about 90° flexion due to flexing of the hamstring muscle of the thigh when the knee is flexed and a resulting force tending to pull the tibia posteriorly.

Preferably, the lateral surfaces of the intercondylar recess of the femoral component and the post of the tibial component are shaped and dimensioned to permit essentially free normal rotation and lateral angulation of the prosthetic joint. To this end, the lateral surfaces of the recess are substantially flat and parallel, and the lateral walls of the post taper toward each other both superiorly and anteriorly to an extent permitting rotation and lateral angulation within normal ranges. The degree of taper superiorly limits the degree of lateral angulation.

More generally, the post of the tibial component and the intercondylar recess of the femoral component replace, mechanically, the cruciate ligaments of the anatomical knee joint at and near full extension and at and near full flexure. In a large part of the mid range of flexure, normal anteroposterior translation, lateral angulation and rotation may occur without engagement between the post and recess. Nonetheless, extreme relative translation, rotation and angulation and, in virtually all events, dislocation are prevented.

For a better understanding of the invention, reference may be made to the following description of an exemplary embodiment, taken in conjunction with the figures of the accompanying drawings.

DESCRIPTION OF EXEMPLARY EMBODIMENTS

Figure 1:
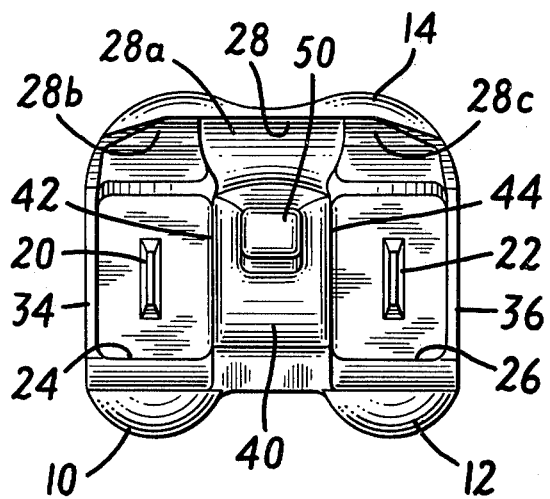
FIG. 1 is a top view of the femoral component of the embodiment.
Figure 4:
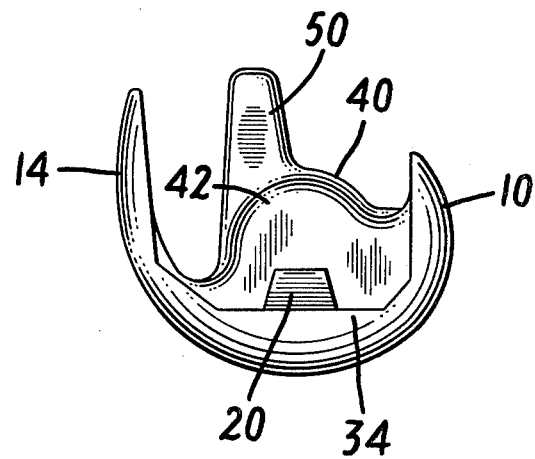
FIG. 4 is a side elevational view of the femoral component.
Figure 2:
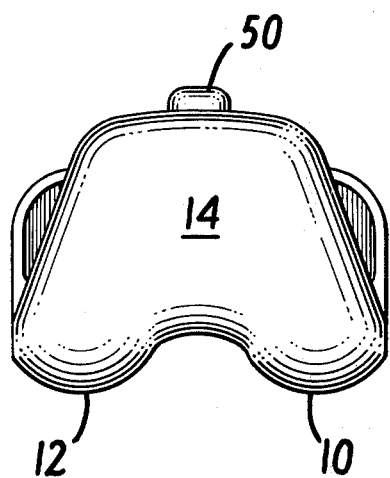
FIG. 2 is a front elevational view of the femoral component.
Figure 3:
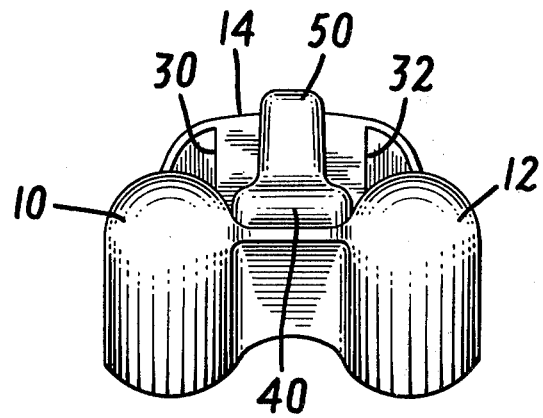
FIG. 3 is a rear elevational view of the femoral component.
Figure 5:
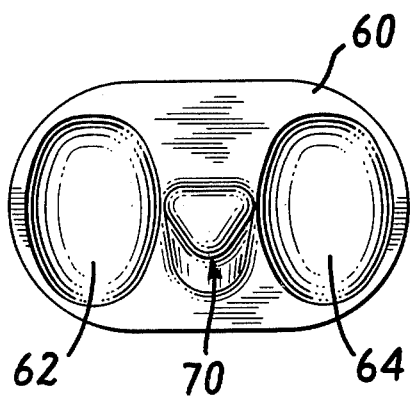
FIG. 5 is a top view of the tibial component of the embodiment.

The femoral component (FIGS. 1 to 4) is preferably made of a surgical grade stainless steel, such as 316L; or a chromecobalt-molybdenum alloy meeting ASTM Standard #F 75–74. All surfaces of the femoral component which are external to the bone, as the prosthesis is implanted, are highly polished. The femoral component is symmetrical about its antero-posterior center plane, thus making it suited for implantation in either the right or left knee of the patient.

The femoral component includes a pair of laterally spaced-apart condylar portions 10 and 12, each of which has in lateral profile (see FIG. 4) a curvature that matches generally the shapes of the anatomical condyles of the femur. The external surface of each condylar portion is convexly curved laterally throughout its antero-posterior extent (see FIGS. 2 and 3). The condylar portions 10 and 12 merge smoothly at their anterior extremities into a patellar portion 14 which has spaced-apart lateral portions that are convexly curved and a medial portion that merges smoothly with the lateral portions and is concavely curved (see FIG. 1). The inferior parts of the internal surfaces of the condylar portions 10 and 12 are flat and lie generally horizontally, and a small fixation rib 20, 22 projects up from each such surface. The internal surfaces 24 and 26 of the posterior parts of the condylar portions 10 and 12 are generally flat and lie generally vertically. The internal surface 28 of the patellar portion 14 includes a generally flat sloping medial portion 28a which curves inferiorly and posteriorly near its inferior extremity and somewhat more steeply sloped internal, lateral surfaces 28b and 28c on either side of the medial portion, thus to form shoulders 30 and 32. Small ribs 34 and 36 extend along the lateral, internal edges of the condylar portions 10 and 12 and the patellar portion 14. The ribs 34 and 36 and the various flats and shoulders on the interior surfaces of the condylar portions and patellar portion assist in properly locating the femoral component upon implantation, facilitate reasonably precise bone resection during the surgical implantation procedure and provide facets and peripheral structures for firm and durable fixation of the femoral component on the femur.

Figure 10:
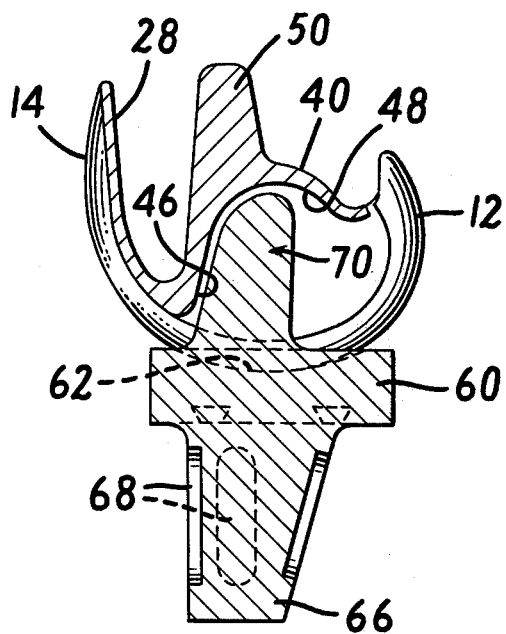
FIGS. 10, 11 and 12 are side cross-sectional views illustrating the assembled prosthesis at full extension, about 45° flexure and about 90° flexure, respectively.
Figure 11:
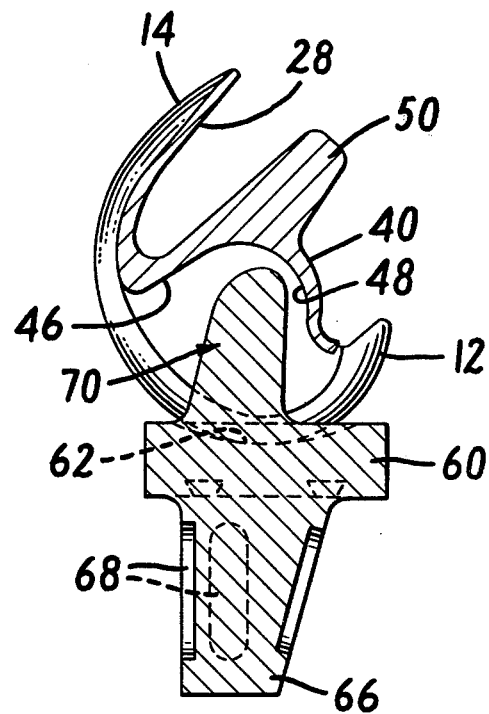
Figure 12:
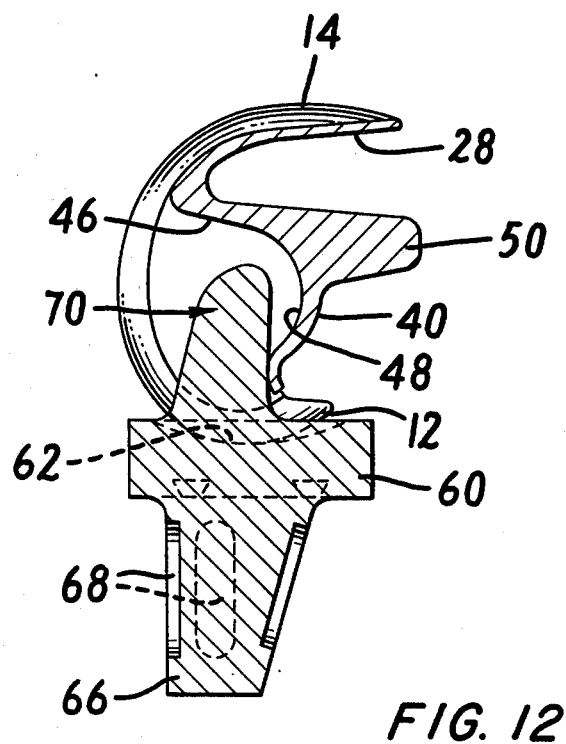

The condylar portions 10 and 12 of the femoral component are interconnected by an intercondylar portion 40 which is of generally dome-like or box-like configuration. The intercondylar portion 40 includes spaced-apart lateral walls 42 and 44 which are flat and parallel and are joined to the inner edges of the inferior and posterior parts of the respective femoral condylar portions 10 and 12, an anterior wall 46 which extends up from the inferior, medial part of the patellar portion 14 (see particularly FIGS. 10 to 12) and a posterior wall 48 which is joined at its posterior edge to the superior, internal edge portions of the condylar surfaces 10 and 12. The walls (42, 44, 46 and 48) of the intercondylar portion 40 define an intercondylar recess which is open throughout the inferior and posterior extent of the intercondylar part of the component. A fixation post 50 extends up from generally the anterior part of the intercondylar portion 40.

Figure 8:
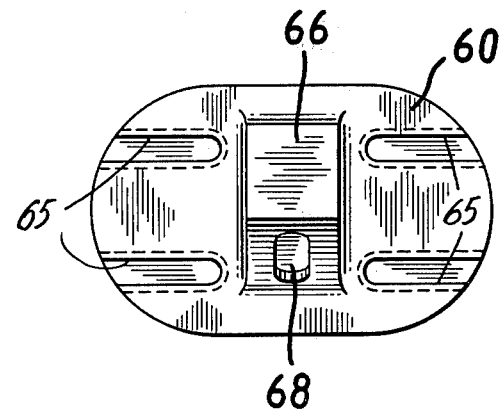
FIG. 8 is a bottom view of the tibial component.
Figure 6:
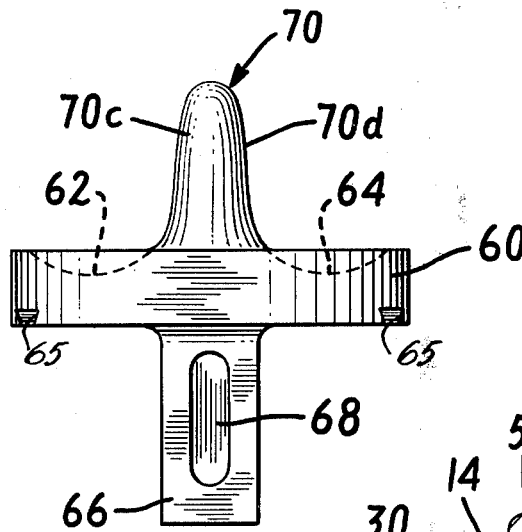
FIG. 6 is a front elevational view of the tibial component.
Figure 7:
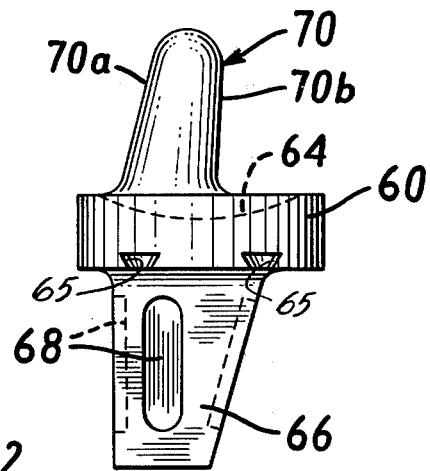
FIG. 7 is a side elevational view of the tibial component.
Figure 9:
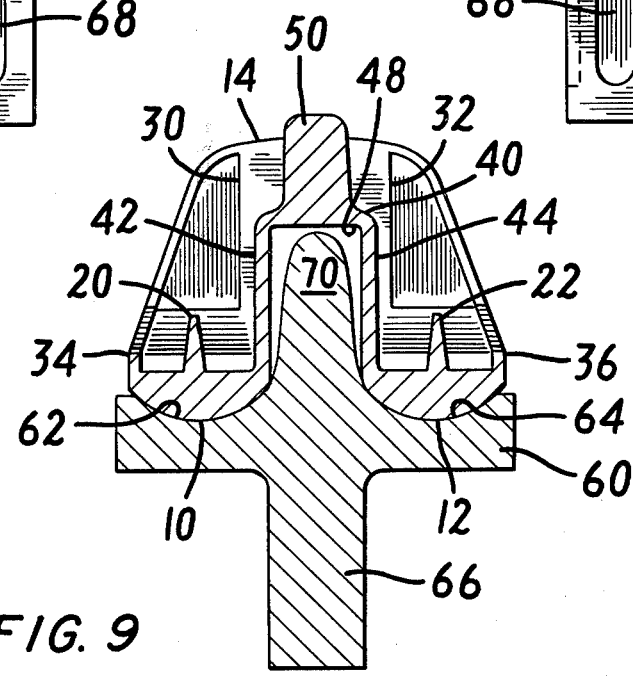
FIG. 9 is a rear transverse cross-sectional view of the embodiment illustrating the components in assembled position at full extension of the leg.

The tibial component (FIGS. 5 to 8) is preferably made of a surgical grade, low-friction, high-density, low-wearing plastic, such as RCH-1000, and is symmetrical about a vertical center plane. It includes a generally plate-like platform portion 60 having a pair of laterally spaced-apart concavities 62 and 64 on its external or superior surface and two pairs of dovetail slots 65 on its inferior surface (see FIG. 8). Each of the concavities 62 and 64 has an antero-posterior curvature that is slightly less than the minimum curvature in the antero-posterior direction of the condylar portions 10 and 12 of the femoral component and also has a lateral curvature that is slightly less than the corresponding lateral curvatures of the femoral condylar portions, thus to facilitate translation and rotation of the femoral component. A relatively large keel-like fixation post 66 extends down from the underside of the platform portion 60 and has slots 68 in each of its side faces and in the front and rear faces which, upon implantation, receive bodies of cement and firmly anchor the tibial component to the tibia. Similarly, the dovetail slots in the under surface of the platform portion receive cement and contribute to strong, durable fixation.

A post 70 extends up from the medial portion of the superior surface of the platform portion 60. The anterior 70a of the post 70 is rounded and slopes slightly posteriorly (see FIG. 7). The posterior 70b of the post is generally flat and slopes very slightly posteriorly. The top of the post is rounded.

As is well known to those skilled in the art, the components of the prosthesis are implanted in the femur and tibia by a surgical procedure which involves resection of bone on condyles of the femur and tibia and formation of holes to receive the fixation posts. The components are then implanted and strongly and durably affixed to the bones by a surgical cement, such as polymethyl methacrylate.

The prosthesis, as implanted in the reconstructed knee joint, permits substantially the full function provided by the anatomical knee joint. In all positions of the leg, the external surfaces of the condylar portions 10 and 12 of the femoral component rotate in the concavities 62 and 64 of the tibial component, and the post 70 of the tibial component extends up into the intercondylar recess of the femoral component. Throughout the range of movement of the leg, the prosthesis permits relatively free normal rotation and lateral angulation; to this end the lateral surfaces of the tibial post are slightly spaced from the lateral walls of the intercondylar recess of the femoral component, and a slight taper superiorly of the lateral surfaces 70c and 70d of the post and the lateral clearance between the post and the walls of the intercondylar recess permit lateral angulation, but at the same time the relatively close spacing between the surfaces of the post and the walls of the intercondylar recess and the taper prevent excess lateral angulation. The lateral surfaces 70c and 70d of the post also taper anteriorly, thus to permit rotation.

At full extension (FIG. 10) there is a slight clearance between the anterior surfaces of the post and recess when the femoral component is fully seated in a "bottomed-out" position of the femoral condylar surfaces in the tibial condylar concavities of the tibial component. However, a small posterial displacement of the femoral component, relative to the tibial component, will bring the anterior surfaces of the post and recess into engagement, thereby preventing further posterial movement of the femoral component relative to the tibial component. Accordingly, posterior dislocation of the femur relative to the tibia is prevented. The slope of the anterior of the post relative to the vertical is greater than the slope of the anterior of the recess; accordingly, at full extension, it is the inferior edge of the anterior wall of the recess which engages the anterior of the post. Thus, any forces exchanged at and near full extension between the femoral component and tibial component are exchanged close to the platform portion of the tibial component and, therefore, the risk of the tibial component being subject to a large force acting at a substantial distance from the platform portion, and thus acting with a leverage, is at full extension considerably less than in the hinge type and certain other forms of prostheses that are designed to provide a high degree of stability to the prosthetic knee joint. Also the difference in the slopes of the anterior surfaces of the post and recess permits hyper-extension of the knee joint.

Throughout the lower range of leg flexure (between FIGS. 10 and 11), the potential for engagement between the anterior surfaces of the post and recess of the prosthesis persists, but to an increasingly lesser degree, the greater the flexure. In other words, in the lower range of flexure, the prosthesis continues to be capable of preventing posterior displacement of the femur relative to the tibia by means of engagement between the anterior surfaces of the post and recess, and of course posterior dislocation is impossible in all but a radical and highly traumatic axial separation, an extremely unlikely event that would not occur in any circumstance other than a serious accident. Throughout the mid range of flexure (FIG. 11), there is a potential for engagement between the top of the post and the juncture between the anterior and posterior surfaces 46 and 48 of the intercondylar recess of the femoral component, but in general, normal antero-posterior relative translation of the component is permitted. Only extreme anterial or posterial movements are prevented by engagement between the post and recess.

As the degree of flexure approaches full flexure (see FIG. 12), the inferior extremity of the posterior wall of the recess of the femoral component approaches more closely the postero-inferior part of the posterior surface of the post. Accordingly, the prosthesis increasingly restricts anterial displacement of the femoral component relative to the tibial component. In other words, as the leg moves closer to full flexure, the degree of anterior displacement of the femoral component which is possible without engagement between the postero-inferior surfaces of the post and recess becomes less, and throughout the higher range of flexure, therefore, the prosthesis provides increasing restriction against anterial translation of the femur relative to the tibia and in all events prevents anterior dislocation of the femur.

I claim:

1. A knee joint prosthesis comprising a femoral component adapted to be implanted on the condylar portion of the femur and having a pair of laterally spaced-apart condylar portions, each of which has an external surface that is smoothly convexly curved in the antero-posterior direction and generally matches the shapes in lateral profile of the condylar surfaces of the femur and that is smoothly convexly curved in all cross sections along its antero-posterior extent, and a box-like intercondylar portion interconnecting the condylar portions and defining an intercondylar recess having spaced-apart lateral surfaces, an anterior surface and a posterior surface; and a tibial component adapted to be implanted on the tibial plateau and including a plate-like platform portion having on its superior surface a pair of laterally spaced-apart concavities, each of which is adapted to receive in nested relation one of the condylar portions of the femoral component, and a post extending superiorly from the platform portion which is adapted to be received in the intercondylar recess of the femoral component, the post having lateral surfaces, an anterior surface and a posterior surface, the relative positions and shapes of the anterior surfaces of the post and recess of the prosthesis as implanted in the knee joint being such that when the leg is at and near full extension and the femur tends to dislocate posteriorly relative to the tibia, the anterior surfaces engage each other to prevent posterial dislocation of the femoral component and when the leg is partly flexed the anterior surfaces are spaced from each other and permit relatively free relative antero-posterior translation of the components but restraining excessive anterior and posterior movements, the relative positions and shapes of the posterior surfaces of the post and recess of the prosthesis as implanted in the knee joint being such that when the leg approaches full flexure and the femur tends to dislocate anteriorly, the posterior surfaces engage each other to prevent anterial dislocation of the femoral component and when the leg is partly flexed or is extended the posterior surfaces are spaced-apart and permit essentially free, relative antero-posterior translation of the components, and the adjacent lateral surfaces of the post and recess diverging superiorly relative to the platform portion of the tibial component to permit essentially free normal lateral angulation.

2. A knee joint prosthesis according to claim 1, wherein in the assembled prosthesis the adjacent lateral surfaces of the post and recess diverge anteriorly to permit essentially free normal rotation.

3. A knee joint prosthesis according to claim 1, wherein the lateral surfaces of the intercondylar recess of the femoral component are substantially flat and parallel and the lateral surfaces of the post of the tibial component taper toward each other both superiorly and anteriorly, thus to afford rotation and lateral angulation of the prosthetic joint.

4. A knee joint prosthesis according to claim 1, and further comprising an upwardly extending patellar portion having an anterior external surface shaped substantially to match the anatomical patellar surface of the femur and curving smoothly along its interior portion to merge with the condylar portions and the intercondylar portion.

* * * * *